(12) United States Patent
Machado et al.

(10) Patent No.: US 7,798,024 B2
(45) Date of Patent: Sep. 21, 2010

(54) MODULAR SYSTEM FOR INTERNAL INSPECTION OF STORAGE TANKS CONTAINING LIQUID FUELS

(75) Inventors: Alander Ornellas Machado, Niterói (BR); Mauro Iurk Rocha, Niterói (BR); Ricardo Rodrigues da Cunha Pinto, Rio de Janerio (BR); Ney Robinson Salvi dos Reis, Rio de Janeiro (BR); Marco Antônio Meggiolaro, Rio de Janeiro (BR); Felipe dos Santos Scofano, Rio de Janeiro (BR)

(73) Assignee: Petróleo Brasileiro S.A.-Petrobras, Rio de Janiero (BR)

( * ) Notice: Subject to any disclaimer, the term of this patent is extended or adjusted under 35 U.S.C. 154(b) by 391 days.

(21) Appl. No.: 11/797,822

(22) Filed: May 8, 2007

(65) Prior Publication Data

US 2008/0025881 A1    Jan. 31, 2008

(30) Foreign Application Priority Data

Jul. 28, 2006    (BR) .................................... 0603020

(51) Int. Cl.
*G01N 19/00* (2006.01)
(52) U.S. Cl. .................................... 73/865.9
(58) Field of Classification Search .................. 73/865.9
See application file for complete search history.

(56) References Cited

U.S. PATENT DOCUMENTS 5,956,077 A * 9/1999 Qureshi et al. ................ 348/82
2006/0117837 A1* 6/2006 Voglsinger .................. 73/40.7

FOREIGN PATENT DOCUMENTS

EP    1 156 304    11/2001

* cited by examiner

*Primary Examiner*—Hezron Williams
*Assistant Examiner*—Alex Devito
(74) *Attorney, Agent, or Firm*—Nixon & Vanderhye PC

(57) ABSTRACT

A modular system used to visually inspect the interior of storage tanks and to simultaneously collect samples to analyze the products stored. The modular internal inspection system includes an assembly made up by a pneumatic controller (2), a pneumatic module (3), an interface module (4), a control module (5), an operation module (6), and several connection cables (7a, 7b, 7c). The system may be remotely operated and allows recording the images and the data collected during inspection. The modular internal tank inspection system is used in storage tanks (1) of any geometric configuration, normally found in industrial installations. Furthermore, because it is an intrinsically secure system, it may be used on tanks that store different types of liquid fuels, with no risk of explosion.

8 Claims, 3 Drawing Sheets

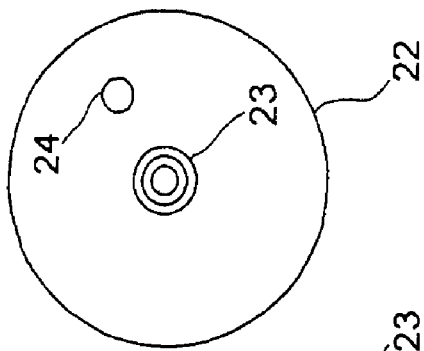
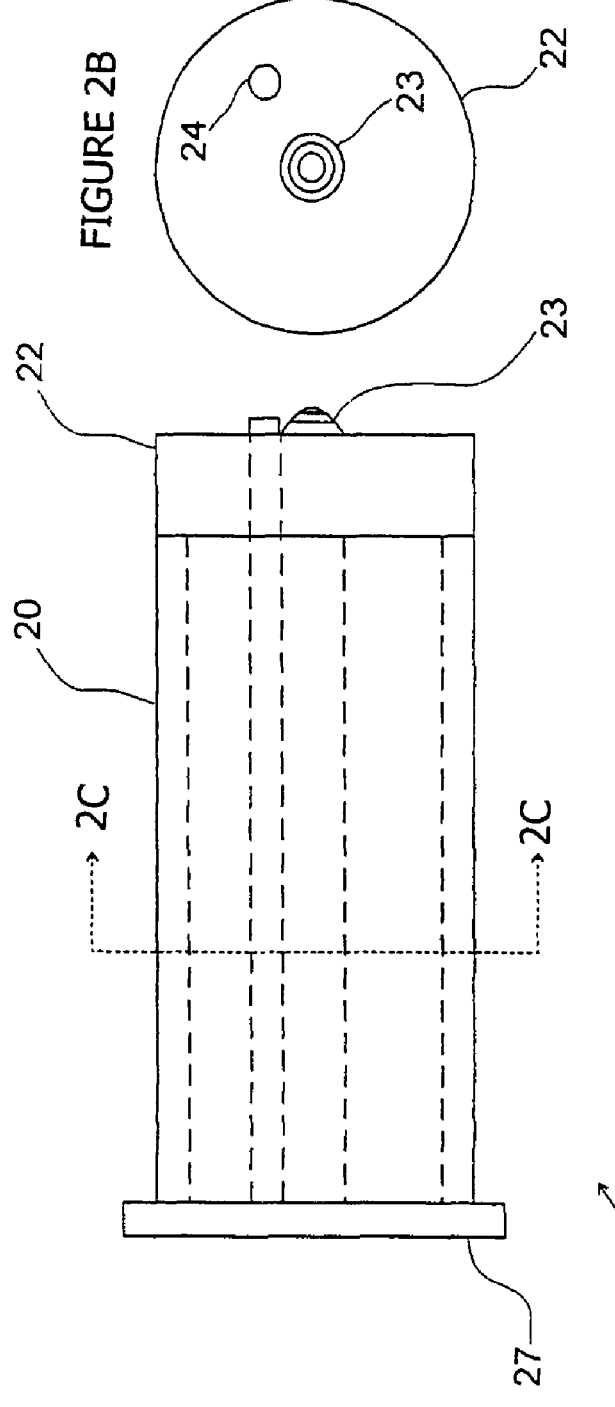
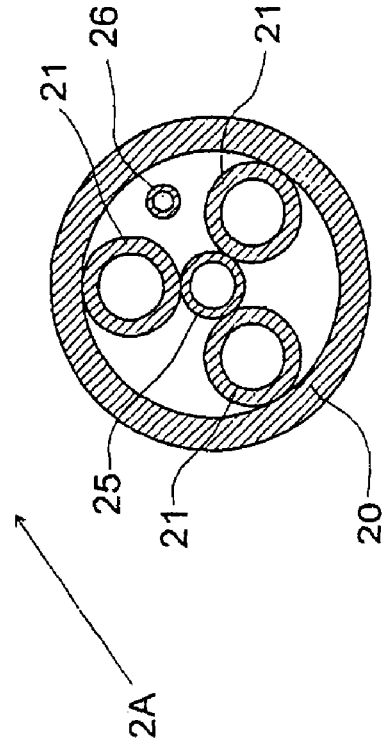

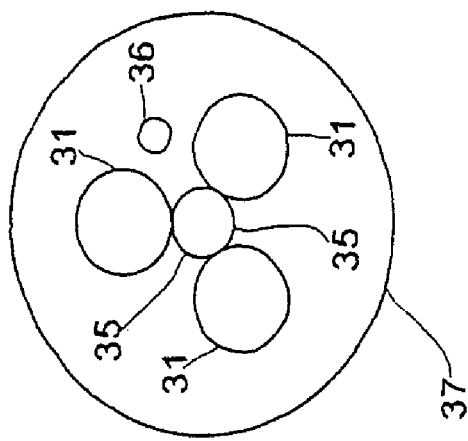
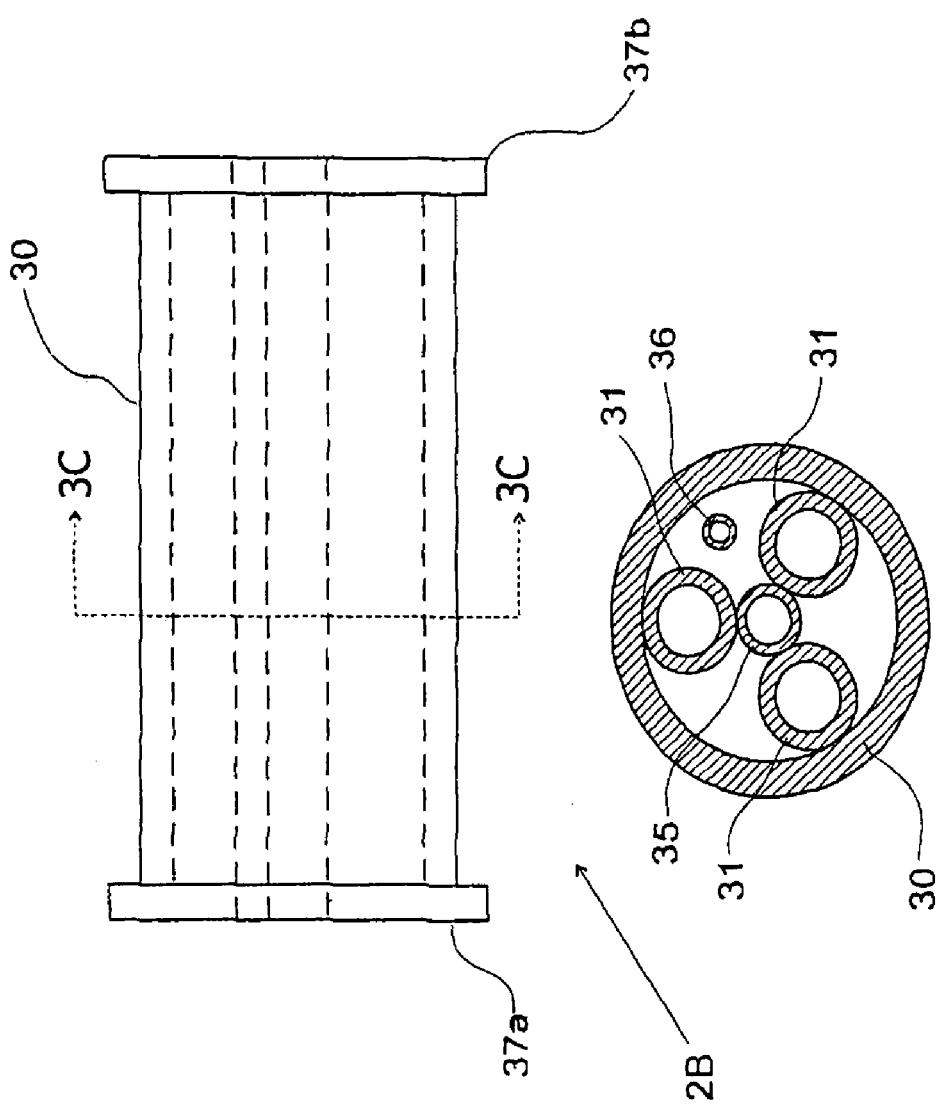

MODULAR SYSTEM FOR INTERNAL INSPECTION OF STORAGE TANKS CONTAINING LIQUID FUELS

CROSS REFERENCE TO RELATED APPLICATION

This application is based upon, claims the benefit of, priority of, and incorporates by reference, the contents of Brazilian Patent Application No. PI 0603020-3 filed Jul. 28, 2006.

BACKGROUND OF THE INVENTION

This invention refers to a system to perform an internal inspection of storage tanks containing liquid fuels. The function of said system is to inspect the inside of the tank through capturing images in real time and to collect selected samples of the stored material and other foreign materials to be analyzed. Said functions are remotely controlled by an operator located nearby and outside of the tank to be inspected.

Storage of liquid fuel in tanks occurs at various stages in the logistical chain of production, distribution, and marketing. Said products are stored in tanks installed in refineries, in terminals, in distribution bases, in large consumer warehouses, and in service and gas stations.

In each of these locations a different type of tank geometry and storage period is used. During this storage period, the product may be contaminated with other types of products or water itself coming from humidity in the air inside the tank, from rainwater entering the tank, from improper handling, from accidental contamination, or from the production process itself.

In an effort to preserve the characteristics of the stored products, to avoid damages and possible contamination to the environment, it is advisable to adopt a cleaning and inspection routine of the tanks where these liquid products are stored. Usually, inspections are very arduous, since they involve emptying the tank completely before the service can be performed, which can result in high direct and indirect costs. In addition to the characteristics of the product, the inspection of the internal parts of the storage tanks allows verification of its walls regarding the appearance of possible points of corrosion and/or deterioration of the inner lining, when applicable.

Currently, it is not possible to precisely know when certain tanks need to be submitted to a cleaning procedure without emptying it. Said lack of precision, however, may cause a loss of time and money since, with this method, many storage tanks are subject to being emptied in order to inspect the inner parts, at a time that may be too soon, even if it is in good condition, which causes unnecessary costs, or too late, which compromises the quality of the stored fuel and the integrity of the tank itself.

The determination of the precise moment at which it is necessary to perform a cleaning of the storage tank allows a significant reduction in the cost of operation in a storage system, which avoids the expense of unnecessary down time and also allows for identifying the presence of contamination in the storage tanks, which may cause product and materials degradation. This problem may be solved by using an inspection system by capturing images in real time from the inside of the tank, as well as collecting samples to be analyzed for any foreign materials that might be inside the tank. Such a system must permit precise positioning of the inspection devices and collecting samples inside the storage tanks. It must also be flexible enough for movement inside the entire tank, independent from the volume of the stored product inside of the storage tank, and be capable of being remotely operated.

Related Technique

At this moment, no system capable of permitting an inspection from any position within the storage tank and simultaneously collecting samples of the stored contents is known. Currently it is only possible to collect samples of liquid fuel and foreign materials by draining and sampling and that are not capable of acting on the entire contents in the tanks, or that reduce the possibility to detect localized problems.

European patent EP 1 156 304 A1 describes a visual inspection system of tanks which includes a viewing unit, a lighting device, a device to capture images and a remote viewing device. The viewing unit is found on the end of one of the inspection system arms. Inside said viewing unit are introduced: a lighting device and the image capturing device. Said image capturing device is connected to the remote viewing device by the operator, which controls the inspection of the tank.

The system described by patent EP 1 156 304 A1 presents two great disadvantages. The first refers to the fact that the viewing device needs to be rigid and not modular, which limits its use in large sized or irregular shaped tanks, since areas that are distant from the observation device are hard to see. The other disadvantage refers to the fact that there is no system for sample collection, which is fundamental for determining the proper time to perform maintenance on the storage tanks.

SUMMARY OF THE INVENTION

The solution proposed by this invention, attempts to allow visual inspection and sample collection through a flexible pneumatic controller, adapted and graded to perform inspections in liquid fuel storage tanks. This system, the base of which is installed through an opening in the top of the tank, usually known as "view aperture" or "inspection aperture", make the inspection of all the walls and all the internal volume possible, for any condition of measuring the liquid in the tank. The pneumatic controller allows positioning a device to view the appearance of the inside of the tank in any area, and to collect samples of the stored liquid fuel and other foreign material.

This invention presents a system for the internal inspection of storage tanks, controlled and monitored remotely, which permits simultaneously viewing and capturing images in real time and collecting samples at any area inside the tank during the inspection. Such system includes a pneumatic controller, a pneumatic module, an interface module, a control module, and an operation module. The system presented in this document has the following principal advantages: allows viewing and collecting samples in any area inside the tank, possesses a modular construction, and it is an intrinsically secure system. Because it is a modular system it may be used in any type of tanks normally found in industrial installations, and because it is a system intrinsically secure, it may be used in tanks that are used to store the most diverse types of liquid fuels and other flammable liquids, with no risk of explosion.

This invention refers to a modular system for inspecting the interior of liquid fuel storage tanks, used to inspect visually the inside of the tank and to collect samples to analyze the stored products.

The internal tank inspection system includes a pneumatic controller, a pneumatic module, an interface module, a control module, an operation module, and several connection cables. The internal tank inspection system may be operated remotely and allows for recording, the images and the data collected during inspection. The internal tank inspection system has a modular construction and its pneumatic controller may be mounted at the desired extension, which allows it to be used on any of the storage tanks commonly found in industrial installations. Furthermore, since it is an intrinsically secure system, because it is constructed of a material that is resistant to the stored product and is spark-proof, the internal tank inspection system may be used in tanks that store the most diverse types of liquid fuel, with no risk of explosion.

BRIEF DESCRIPTION OF THE DRAWINGS

The invention shall now be explained in greater detail, together with the figures related below, merely as an example, which follow this report as an integral part, and in which:

FIGS. 2A-C show a front view, a side view, and a cross section of the terminal module, that is the preferred implementation of this invention.

FIGS. 3A-C show a front view, a side view, and a cross section of the extension module, that is the preferred implementation of this invention.

DETAILED DESCRIPTION OF THE INVENTION

Figure 1:
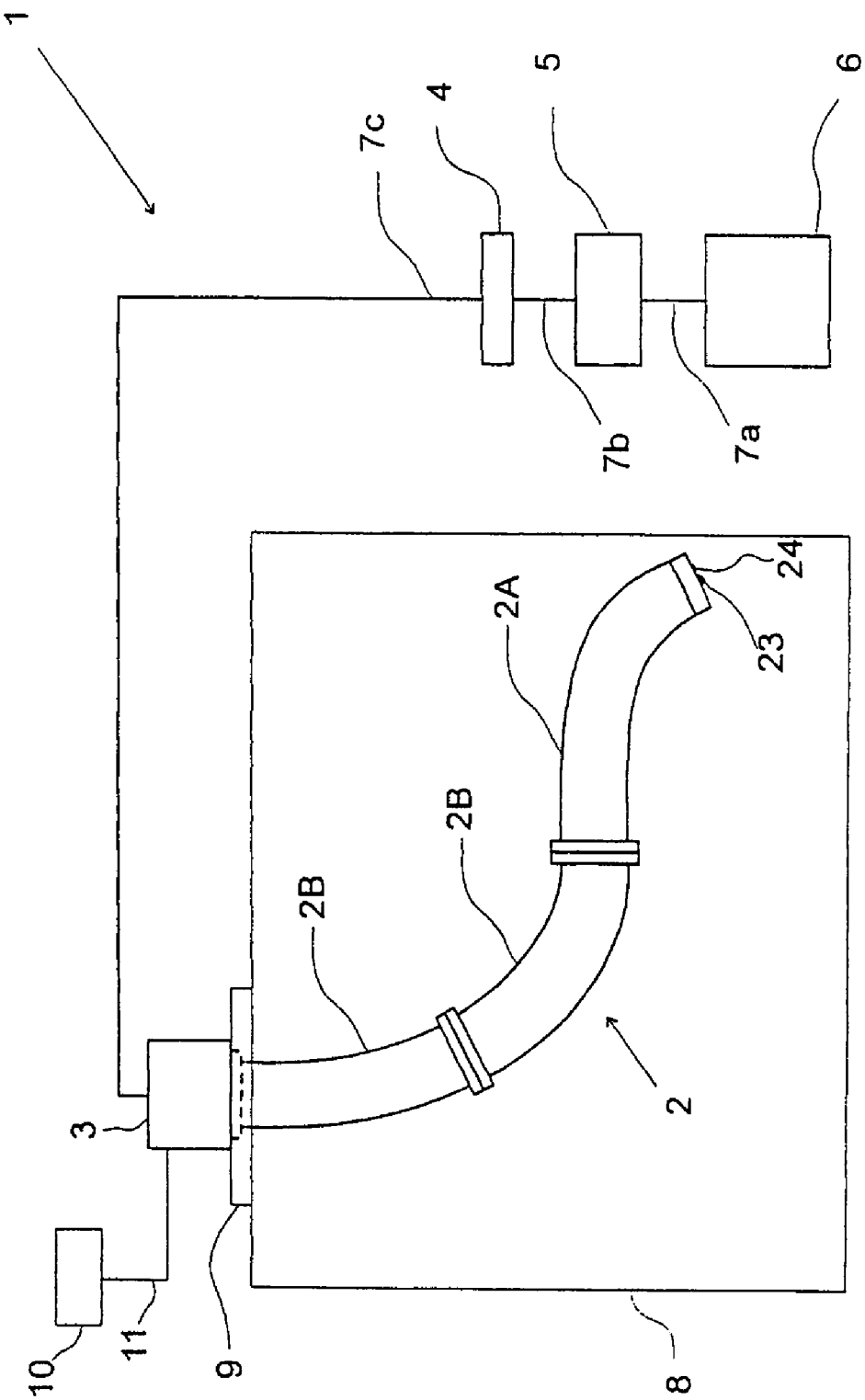
FIG. 1 shows a diagram of the preferred implementation of the internal tank inspection system.

FIG. 1 shows a preferred implementation of the internal inspection system for storage tanks (1), which includes a pneumatic controller (2), a pneumatic module (3), an interface module (4), a control module (5), an operation module (6), and several connection cables (7). The operation module (6) allows the operator to control the positioning of the pneumatic controller (2), to control the operation of sample collection, to view the inside of the tank (8), and to record the data that is transferred by the internal storage tank inspection system (1). The interaction between the operator and the inspection system occurs through a dedicated computer program that translates the movement commands emitted by the operator to be executed by the inspection system. There is a mathematic model added to this computer program supported by a number of specific equations to that end. Said operation module (6) is interlinked to the control module (5) by a connecting cable (7a). The control module (5) receives the information from the operation module (6), processes these and sends an actuator signal to the interface module (4). The interface module (4) receives the actuator signal, processed by the control module (5), through a connecting cable (7b), and it converts it into the proper pattern of activation for the pneumatic module (3). Said signal, processed by the interface module (4) is sent through the connecting cable (7c) to the pneumatic module (3). The pneumatic module (3), which receives gas from a gas supply source (10), through a supply line (1 1), which regulates pressure and the gas output into the inside of the pneumatic controller (2). The pneumatic controller (2) allows positioning an image capturing device (23) and one or more sample collecting device (24) inside the tank (8).

The pneumatic controller (2) includes a terminal module (2A) and a number of extension modules (2B). The number of extension modules (2B) varies with the size and geometry of the tank (8) to be inspected, whose mould is defined by a dedicated computer program to allow the movements of the system be properly coordinated. Therefore, the number of extension modules (2B), presented in FIG. 1, that shows the preferred implementation for the internal storage tank inspection system (1), should not be considered as a limitation for this invention. It should be noted that the tank (8), its view aperture (9), the gas supply source (10) and the supply line (11) are not part of the invention and they are shown in FIG. 1 in order to permit a better understanding of how it operates. It should even be noted that the internal tank inspection system (1) should have an electrical supply from an external source, not shown in FIG. 1, in order for it to run.

The connecting cables (7a, 7b e 7c) have the function to allow the transmission of analogue or digital signals between the pneumatic module (3), the interface module (4), the control module (5), and the operation module (6).

In this way, modules (4, 5, 6) may form one single component, for example, a computer with proper output plates linked by a cable to the module (3).

As can be seen in FIGS. 2A-C, the terminal module (2A) of the pneumatic controller (2) includes a clad tube of the terminal module (20), a number of pneumatic chambers of terminal module (21), a central tube of terminal module (25), a collecting tube of the terminal module (26), an intermediary connection of the terminal module (27) and a terminal connection (22). Said terminal connection (22) houses an image capturing device (23) and a sample collecting device (24).

As can be seen in FIGS. 3A-C, the components of the extension module (2B) of the pneumatic controller (2) are similar to the terminal module (2A). Thus, the extension module (2B) includes a clad tube of the extension module (30), a number of pneumatic chambers of the extension module (31), a central tube of the extension module (35), a collecting tube of the extension module (36), and two intermediary connections (37a and 37b) to join extension module segments (2B).

As mentioned above, the pneumatic controller (2) includes a number of extension module (2B) and a terminal module (2A), connected to each other. The configuration of the pneumatic controller (2) should be defined as a function of the geometry of the tank (8) to be inspected. If the tank is small, the pneumatic controller (2) may be the terminal module (2A) itself.

Once connected, the extension modules (2B) and the terminal module (2A) become one single component, or in other words, the pneumatic controller (2). The pneumatic controller (2) will receive gas in each of pneumatic chambers of terminal module (21) and pneumatic chambers of extension module (31), individually, which will allow a variation of its form and its position within the tank (8). The calculation of the pressure that must be maintained inside each pneumatic chamber of terminal module (21) and each pneumatic chamber of extension module (31), for the definition of the position of the pneumatic controller (2), is made by the control module (5), through a specific computer program for this function. It should be mentioned that the clad tube of terminal module (20) and the clad tube of extension module (30) must be flexible enough to allow the pneumatic controller (2) be deformed. The central tube of the terminal module (25) and the central tube of the extension module (35) give a minimum rigidity to the structure of the pneumatic controller (2).

It is important to highlight that, due to its construction and the materials used, the modular internal tank inspection system (1) of the invention is an intrinsically secure system, since the pneumatic controller (2), which enters into contact with the product stored in the tank (8), does not release any electrical energy and does not produce sparks, that might be caused by friction against the tank walls (8). In this way, the modular internal tank inspection system (1) can be used on tanks that store the most different types of liquid fuels, with no risk of explosion.

The elements that integrate the modular internal tank inspection system (1), the object of this invention, use materials, components, and fixtures known in the state of the art. Therefore, the components of the modular internal tank inspection system (1) may be fastened to each other using bolts, rivets, glue, soldering, or any other method of fastening known in the state of the art. The components of the pneumatic controller (2) may be constructed of an appropriate polymer material, such as polyurethane, commercial products such as viton (fluorinated polyethylene) and Teflon (fluorinated polypropylene), metal alloys or any material, with the mechanical characteristics and physico-chemical properties necessary for carried out their functions. It should be also highlighted that, for the manufacture and assembly of the pneumatic module (3), of the interface module (4), of the control module (5) and of the operation module (6), components used are known in the state of the art, such as valves, connections, printed circuit boards, microprocessors, converter boards, video monitors, keyboards, and [power] sources. However, the assembly now proposed constitutes a new and an innovative set.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. Modular internal inspection system for liquid fuel storage tanks, capable of allowing visual inspection of any internal area, as well as collecting samples of the stored product, characterized by including an assembly constituted by the following components:
    an operation module which allows the operator to control a pneumatic controller, to control the operation of sample collection, to view the inside of the tank, and to record the data that is transferred by the internal tank inspection system;
    a control module that receives the information from the operation module, processes the information and sends an actuator signal to the interface module;
    an interface module which receives the actuator signal, processed by the control module, and converts it into the proper pattern of actuation for the pneumatic module;
    a pneumatic module, which regulates the pressure and the gas output received from a gas supply source, into the inside of the pneumatic controller;
    a number of connecting cables;
    the pneumatic controller comprises:
        a) terminal module which includes a clad tube of the terminal module, a number of pneumatic chambers of the terminal module a central tube of the terminal module, a collection tube of the terminal module, an intermediary connection of the terminal module and a terminal connection, which houses an image capturing device, and a sample collecting device.

2. Modular internal inspection system for liquid fuel storage tanks in accordance with claim 1, characterized by the interface module, the control module, and the operation module form one single component which are interlinked to the pneumatic module by connecting cables.

3. Modular internal inspection system for liquid fuel storage tanks in accordance with claim 1, characterized, by the interface module, the control module, and the operation module form one single component being that single component interlinked to the pneumatic module by a connecting cable.

4. Modular internal inspection system for liquid fuel storage tanks in accordance with claim 1, characterized by the pneumatic module, the interface module, the control module, and the operation module forming one single component.

5. Modular internal inspection system for liquid fuel storage tanks in accordance with claim 1, characterized by being remotely operated and allowing record of images and data collected during the inspection.

6. Modular internal inspection system for liquid fuel storage tanks in accordance with claim 1, characterized by the interaction between the operator and the inspection system to occur through a dedicated computer system that translates the movement orders transmitted by the operator to be executed by the inspection system.

7. Modular internal inspection system for liquid fuel storage tanks in accordance with claim 1, characterized by the pneumatic controller further including a number of extension modules, each one of which includes a clad tube of the extension module, a number of pneumatic chambers of the extension module, a central tube of the extension module, a collecting tube of the extension module, and two intermediate connections of the extension module.

8. Modular internal inspection system for liquid fuel storage tanks in accordance with claim 7, characterized by the terminal module clad tube, and the extension module clad tube, being flexible enough to allow the pneumatic controller to bend and which are made from appropriate polymeric materials in order to function properly when in use and be resistant to the stored product.

* * * * *